US011696820B2

(12) United States Patent
Ladet et al.

(10) Patent No.: US 11,696,820 B2
(45) Date of Patent: *Jul. 11, 2023

(54) HERNIA PROSTHESIS WITH MARKING MEANS

(71) Applicant: SOFRADIM PRODUCTION, Trevoux (FR)

(72) Inventors: Sébastien Ladet, Caluire & Cuire (FR); Sebastien Francois, Jassans-Riottier (FR); Nicolas Prost, Orlienas (FR)

(73) Assignee: SOFRADIM PRODUCTION, Trevoux (FR)

( * ) Notice: Subject to any disclaimer, the term of this patent is extended or adjusted under 35 U.S.C. 154(b) by 377 days.

This patent is subject to a terminal disclaimer.

(21) Appl. No.: 17/002,401

(22) Filed: Aug. 25, 2020

(65) Prior Publication Data

US 2020/0383765 A1   Dec. 10, 2020

Related U.S. Application Data

(63) Continuation of application No. 15/963,388, filed on Apr. 26, 2018, now Pat. No. 10,820,979, which is a continuation of application No. 14/366,403, filed as application No. PCT/EP2012/076982 on Dec. 27, 2012, now Pat. No. 9,974,641.

(30) Foreign Application Priority Data

Dec. 29, 2011 (FR) ..................................... 11/62536

(51) Int. Cl.
*A61F 2/00* (2006.01)

(52) U.S. Cl.
CPC .... *A61F 2/0063* (2013.01); *A61F 2250/0097* (2013.01)

(58) Field of Classification Search
CPC ....................... A61F 2/0063; A61F 2250/0097
See application file for complete search history.

(56) References Cited

U.S. PATENT DOCUMENTS

| 5,147,374 A | 9/1992 | Fernandez |
| 5,370,650 A | 12/1994 | Jonathan et al. |

(Continued)

FOREIGN PATENT DOCUMENTS

| FR | 2864443 A1 | 7/2005 |
| FR | 2914179 A1 | 10/2008 |

(Continued)

OTHER PUBLICATIONS

Australian Examination Report dated Jul. 28, 2016 in corresponding Australian Patent Application No. 2012360856, 3 pages.

(Continued)

*Primary Examiner* — Julian W Woo
(74) *Attorney, Agent, or Firm* — Weber Rosselli & Cannon LLP

(57) ABSTRACT

Prosthesis (1) comprising a patch (2) made of biocompatible material, said patch having a generally plane geometric shape that defines two opposite faces, a centre, a length and a width of said patch, characterized in that said patch is provided, on one (2a) of its faces, with a single marking means (3) designed to indicate both the centre (C) of the patch and also the longitudinal direction of said patch.

20 Claims, 1 Drawing Sheet

(56) References Cited

U.S. PATENT DOCUMENTS

| | | |
|---|---|---|
| 6,432,074 B1 | 8/2002 | Ager et al. |
| 6,551,356 B2 | 4/2003 | Rousseau |
| 6,596,002 B2 | 7/2003 | Therin et al. |
| 6,610,006 B1 | 8/2003 | Amid et al. |
| 6,800,082 B2 | 10/2004 | Rousseau |
| 7,011,688 B2 | 3/2006 | Gryska et al. |
| 7,105,001 B2 | 9/2006 | Mandelbaum |
| 8,579,922 B2 | 11/2013 | Glick et al. |
| 8,579,924 B2 | 11/2013 | Stopek et al. |
| 8,821,585 B2 | 9/2014 | Pfeiffer et al. |
| 9,387,280 B2 | 7/2016 | Brunelle et al. |
| 9,974,641 B2 | 5/2018 | Ladet et al. |
| 10,820,979 B2 * | 11/2020 | Ladet .................. A61F 2/0063 |
| 2002/0133236 A1 | 9/2002 | Rousseau |
| 2004/0019360 A1 | 1/2004 | Farnsworth et al. |
| 2005/0288691 A1 | 12/2005 | Leiboff |
| 2007/0299538 A1 | 12/2007 | Roeber |
| 2011/0189270 A1 * | 8/2011 | Broom ................. A61F 2/0063 424/451 |
| 2011/0307077 A1 | 12/2011 | Pfeiffer et al. |

FOREIGN PATENT DOCUMENTS

| | | | |
|---|---|---|---|
| WO | 0207648 A1 | 1/2002 | |
| WO | 03037215 A2 | 5/2003 | |
| WO | 2010059234 A1 | 5/2010 | |

OTHER PUBLICATIONS

Canadian Office Action issued in corresponding Canadian application No. 2,858,002 dated Oct. 12, 2018, 3 pages.

Chinese Office Action and English Translatio, Application No. 201280061897.8 dated Jul. 3, 2015.

CN Office Action dated Feb. 6, 2016 in corresponding CN Patent Application No. 201280061897.8, together with English language translation, 21 pages.

CN Office Action dated May 10, 2016 in corresponding CN Patent Application No. 201280061897.8, together with English language translation, 20 pages.

European Communication dated May 19, 2016 in corresponding European Patent Application No. 12812669.5, 4 pages.

European Office Action dated Jul. 27, 2017 issued in corresponding European Application No. 12812669.5, 8 pages.

International Search Report for PCT/EP12/076982 dated Feb. 18, 2013 (3 pages).

\* cited by examiner

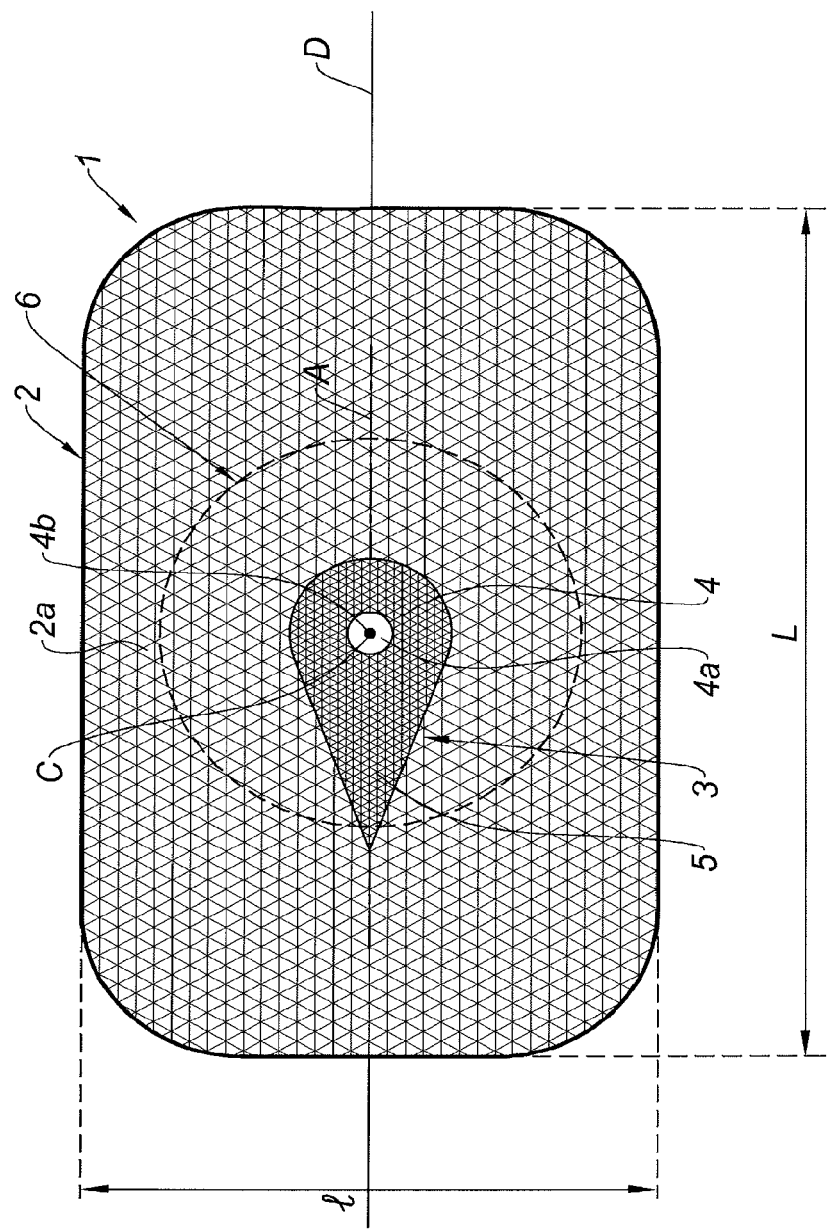
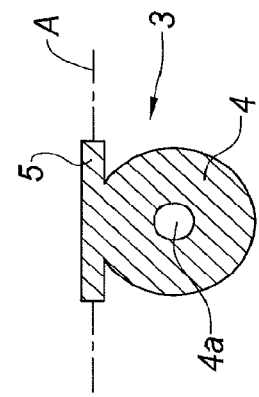
Fig. 1
Fig. 2

HERNIA PROSTHESIS WITH MARKING MEANS

CROSS-REFERENCE TO RELATED APPLICATIONS

This application is a continuation of U.S. patent application Ser. No. 15/963,388, filed on Apr. 26, 2018, which is a continuation of U.S. patent application Ser. No. 14/366,403, filed on Jun. 18, 2014, now U.S. Pat. No. 9,974,641, which is a National Stage Application of PCT/EP2012/076982 under 35 USC § 371 (a) filed on Dec. 27, 2012, which claims benefit of and priority to French Patent Application No. 11/62536 filed Dec. 29, 2011, the disclosures of each of the above-identified applications are hereby incorporated by reference in their entirety.

The present invention relates to a prosthesis, in particular for the repair of hernias, comprising a marking means that makes it easier for the surgeon to fit the prosthesis in place.

A hernia is a phenomenon that causes a tissue defect in a wall of the human body, for example in the abdominal wall. To treat hernias, prostheses have been developed that act as wall reinforcements and that are intended to fill the tissue defect either temporarily or permanently. These prostheses are generally in the form of a patch having a generally plane geometric shape that defines two opposite faces. In the case of a hernia of the abdominal wall for example, one face of the prosthesis is intended to be placed facing the abdominal wall, in order to fill the tissue defect, while the other face is intended to face the abdominal cavity.

These prostheses can be made of porous material, for example a biocompatible openworked textile, with the aim of promoting cell colonization on the face intended to be placed facing the abdominal wall. In such a case, the face intended to be placed facing the abdominal cavity is generally made smooth and non-porous, for example by a coating of an anti-adhesion material, with the aim of avoiding the formation of post-surgical adhesions to the surrounding organs of the abdominal cavity.

Hernia prostheses can have several shapes, for example rectangular, round or oval, depending on the anatomical structure to which these prostheses are intended to adapt. In the case of hernias of the abdominal wall, the nature of the tissue defect that is to be treated means that the prostheses more generally have a shape with a longitudinal dimension, such as a rectangle or an oval. Moreover, the dimensions of these prostheses may vary according to the height and build of the patient and according to the severity of the hernia. Thus, some of these prostheses can have dimensions of up to 42 cm×32 cm, for example.

For reasons of efficacy, these prostheses have to be arranged in a specific and very precise manner in relation both to the defect to be treated and also to the surrounding organs at the time of implantation. It is therefore sometimes useful to provide these prostheses with marking means aimed at giving the surgeon an indication of the particular properties of a face of the prosthesis, of its dimensions, or of the location of a precise point of the prosthesis.

Thus, depending on the environment around the implantation site, for example the presence of viscera, soft tissues, etc., it may be important to provide the surgeon with indications at a given location of the prosthesis, such that the surgeon can arrange the prosthesis in a particular orientation or can arrange a certain region of the prosthesis facing a given organ or, by contrast, as far as possible away from a given organ, etc.

Hernia prostheses comprising markers or means of information already exist.

However, these means of information are not always easily identifiable or visible to the surgeon, especially when the prosthesis is implanted by laparoscopy.

Indeed, when a prosthesis is fitted in place by laparoscopy, the prosthesis is, for example, introduced into the body of the patient by means of a trocar, within which it is generally folded and/or rolled up, and it is then deployed at the implantation site. Although the implantation site is illuminated in this technique by means of another trocar provided for this purpose, and although the surgeon views this site via a camera, the surgical field visible and accessible to the surgeon remains limited. In particular, once the prosthesis has been deployed, it can have a size much greater than the perimeter of this field of view. When the means of information present on the prosthesis are distributed over the whole of the prosthesis, the surgeon is forced to move the latter about in order to find the information for which he is looking, for example in order to identify the face of the prosthesis that is optionally covered with an anti-adhesion material, or in order to locate the centre of the prosthesis, or to determine the longitudinal dimension of the prosthesis so as to position it correctly. In some cases, the surgeon may be forced to move the prosthesis several times in different directions in order to gather all the information he needs. These manoeuvres for moving the prosthesis about mean that time is wasted, and they can also cause confusion when positioning the prosthesis.

There is therefore still a need for prostheses for hernia repair, in particular of the abdominal wall, if appropriate of large dimensions, for example of the order of 42 cm×32 cm, which are provided with means of information that are easily and directly accessible to the surgeon at one glance when fitting these prostheses in place at the implantation site by laparoscopy, these means of information allowing the surgeon to ascertain simultaneously which face of the prosthesis he is dealing with, the location of the centre of the prosthesis and the longitudinal direction of the prosthesis.

The present invention aims to meet this need by making available a prosthesis which is provided, on one of its faces, with a single marking means that is able to indicate both the centre of the prosthesis and also the longitudinal direction of the latter.

The present invention relates to a prosthesis comprising a patch made of biocompatible material, said patch having a generally plane geometric shape that defines two opposite faces, a centre, a length and a width of said patch, characterized in that said patch is provided, on one of its faces, with a single marking means designed to indicate both the centre of the patch and also the longitudinal direction of said patch.

According to the present application, a single marking means is understood as meaning that the marking means, regardless of whether it is continuous or non-continuous, is concentrated on a confined portion of the surface of the face of the patch on which it is present, such that the dimensions of this confined portion are of the order of the dimensions of the surgical field visible to the surgeon when fitting the prosthesis in place by laparoscopy. Thus, when the surgeon looks to find the information he needs in order to position the prosthesis correctly, he does not have to move the prosthesis in several directions, which are sometimes divergent, before positioning the prosthesis in relation to the defect to be treated. According to the invention, the single marking means is able to show the surgeon at just one glance, in the surgical field visible to the surgeon in implantation by laparoscopy, the face of the patch with which the surgeon is dealing, the centre of said patch, and the longitudinal direction thereof, in other words the direction of its length.

In one embodiment of the invention, said marking means is chosen from a sheet of biocompatible material, a coating of a biocompatible material, and combinations thereof.

The sheet of material can be, for example, a film, obtained by extrusion for example, or a textile, or a combination of these. The coating of material can be obtained, for example, by painting on or spraying on a suitable material.

In one embodiment, said marking means has a shape whose perimeter combines the contours of a circular shape and of a generally elongate shape attached to said circular shape, the longitudinal axis of said elongate shape being parallel to the longitudinal direction of said patch in the plane of said patch, and said circular shape comprising a means for identifying its central point, said central point being situated at the centre of said patch.

Thus, when the surgeon sees the marking means in the field of view available to him when fitting the prosthesis of the invention in place by laparoscopy, he obtains the following information directly and at one glance:
the face on which the marking means is situated: the surgeon knows, before implanting the prosthesis, if the marking means is situated on the face of the patch intended to be placed facing the abdominal wall or, on the contrary, on the face of the patch intended to be placed facing the abdominal cavity;
the centre of the patch, generally corresponding to the centre of the prosthesis: the means for identifying the central point of the circular shape shows him the centre of the patch;
the longitudinal direction of the patch, by means of the longitudinal axis of the elongate shape.

For example, said means for identifying the central point of the circular shape is formed by an absence of material in the sheet of material or in the coating of material at the location of the central point of the circular shape.

For example, the elongate shape can have the shape of an arrow, a rod or an elongate triangle. By its nature, the elongate shape has two opposite ends in its longitudinal direction. The elongate shape can be attached to the circular shape via either of its sides or via one of its ends. Preferably, said elongate shape is attached to said circular shape via one of its ends.

In one embodiment, said marking means is made of bioabsorbable material. Such an embodiment makes it possible to limit the amount of foreign material present long-term in the patient's body, while at the same time allowing the surgeon to be provided with the information he needs for correctly positioning the prosthesis at the time of implantation.

Within the context of the present application, "bioabsorbable" or "biodegradable" means the characteristic by which a material is absorbed and degraded by the biological tissues and disappears in vivo after a defined period, which can vary, for example, from a few hours to several months, depending on the chemical nature of the material.

Thus, the bioabsorbable materials suitable for the marking means of the present invention can be chosen from polylactic acid (PLA), polyglycolic acid (PGA), oxidized cellulose, polycaprolactone (PCL), polydioxanone (PDO), trimethylene carbonate (TMC), polyvinyl alcohol (PVA), polyhydroxyalkanoates (PHAs), polyamides, polyethers, copolymers thereof and mixtures thereof.

Alternatively, said marking means can be made of a non-bioabsorbable material. For example, in such an embodiment, the marking means can participate in strengthening the patch forming the prosthesis.

The non-bioabsorbable materials suitable for the marking means of the present invention can be chosen from polyethylene terephthalate (PET), polyamides, aramids, expanded polytetrafluoroethylene, polyurethane, polyvinylidene difluoride (PVDF), polybutyl esters, polyetheretherketone (PEEK), polyolefins (such as polyethylene or polypropylene), copper alloys, silver alloys, platinum, medical grades of steel such as medical-grade stainless steel, and combinations thereof. In some embodiments of the invention, the marking means can be formed from a combination of bioabsorbable material and non-bioabsorbable material.

In one embodiment, said marking means has a colour different than the colour of said patch. Such an embodiment allows the surgeon to immediately and easily locate the marking means when implanting the prosthesis by laparoscopy.

In one embodiment of the invention, said patch is a textile, preferably an openworked textile.

Within the context of the present application, "textile" is understood as any textile obtained from an arrangement or assembly of biocompatible yarns, fibres, monofilaments and/or multifilaments, for example a knit, weave, braid and/or non-woven, and having two opposite faces. According to the present application, "openworked textile" is understood as meaning that, on at least one of its faces, preferably the face intended to be placed facing the abdominal wall, the textile comprises openings, cells, pores or holes, which open to the outside. Such openings promote the penetration of the cells into the textile and thus promote the cell recolonization of the prosthesis after implantation. In one embodiment, both faces of said textile are openworked.

The yarns or fibres or filaments and/or multifilaments forming the textile according to the invention can be made from any biocompatible material, whether bioabsorbable or non-bioabsorbable. The bioabsorbable materials and non-bioabsorbable materials suitable for the yarns forming the textile of the prosthesis patch according to the invention can be chosen from the materials cited above for the marking means.

The textile forming the prosthesis patch according to the invention can be made from completely bioabsorbable yarns if it is intended to disappear after it has performed its reinforcing function during the period of cell colonization and tissue rehabilitation. In other embodiments, it can comprise non-bioabsorbable yarns if the prosthesis is intended to act as a permanent reinforcement and to remain definitively in the body of the patient.

In one embodiment of the invention, the openworked textile of the prosthesis patch according to the invention is a knit. According to the present application, a knit is understood as an arrangement of yarns obtained by knitting. The knit can be two-dimensional or three-dimensional.

Within the context of the present application, a two-dimensional knit is understood as a knit having two opposite faces linked together by meshes but devoid of a spacer: such a knit can be obtained, for example, by knitting yarns on a warp or Raschel knitting machine using two needle-guide bars. Examples of knitting two-dimensional knits suitable for the present invention are given in document WO2009/071998.

According to the present application, a three-dimensional knit is understood as a knit having two opposite faces linked together by a spacer, said spacer itself being formed from additional linking yarns in addition to the yarns forming the two faces of the knit. Such a knit can be obtained, for example, on a double-bed warp or Raschel knitting machine using several needle-guide bars. Examples of knitting three-dimensional knits suitable for the present invention are given in the documents WO99/05990, WO2009/031035 and WO2009/071998.

In one embodiment of the invention, said marking means is a textile, preferably an openworked textile, as has been defined above for the patch forming the prosthesis.

When said patch and said marking means are both textiles, preferably openworked textiles, they can be identical or different. For example, referring to the definitions given hereinabove, said patch can be a three-dimensional knit and said marking means can be a two-dimensional knit.

When said patch and said marking means are both textiles, said marking means can be sewn onto the face of said patch. Alternatively, said marking means can be glued onto the face of said patch.

In one embodiment, said marking means is situated inside a central region of said patch, the surface area of said central region being less than or equal to 20 cm², preferably less than or equal to 16 cm², more preferably less than or equal to 7 cm².

Thus, when fitting the prosthesis in place by laparoscopy the surgeon, without having to move the prosthesis about, is able to discern directly and easily from the single marking means, clearly visible to him within the surgical field, the centre of the prosthesis, the longitudinal direction thereof and the face with which he is dealing.

In one embodiment, said patch, on its face provided with said marking means, is covered with an anti-adhesion coating, said coating likewise covering said marking means. In such an embodiment, the marking means is thus present on the face of said patch forming the face of the prosthesis intended to be placed facing the abdominal cavity.

Within the context of the present application, "anti-adhesion" is understood as referring to a biocompatible material or coating that is smooth and non-porous, provides no space for cell recolonization and prevents the surrounding organs from attaching themselves to the prosthesis.

The anti-adhesion material or coating can be chosen from bioabsorbable materials, non-bioabsorbable materials and mixtures thereof.

The non-bioabsorbable anti-adhesion coatings can be chosen from polytetrafluoroethylene, polysiloxanes, polyurethanes, stainless steels, derivatives of precious metals, and mixtures thereof.

Said anti-adhesion material or coating is preferably bioabsorbable: the bioabsorbable materials suitable for said anti-adhesion coating can be chosen from collagens, for example oxidized collagen, oxidized celluloses, polyacrylates, trimethylene carbonates, caprolactones, dioxanones, glycolic acid, lactic acid, glycolides, lactides, polysaccharides, for example chitosans, polyglucuronic acids, hyaluronic acids, dextrans, fucans, polyethylene glycol, glycerol and mixtures thereof.

Upon implantation of the prosthesis according to the invention, the anti-adhesion coating makes it possible, at least during the initial phase of healing, to protect the textile of the prosthesis at the place where this anti-adhesion coating is present; thus, the covered face is not exposed to inflammatory cells such as granulocytes, monocytes, macrophages or even the multi-nuclear giant cells that are generally activated by the surgery. Indeed, at least during the initial phase of healing, the duration of which can vary between 5 and 10 days approximately, only the anti-adhesion coating can be accessed by the various factors such as proteins, enzymes, cytokines or cells of the inflammatory line.

In the case when the anti-adhesion coating is made of non-absorbable materials, it thus protects the textile before and after implantation, throughout the period of implantation of the prosthesis.

Moreover, by virtue of the anti-adhesion coating, the surrounding fragile tissues, for example the hollow viscera, are protected, in particular from the formation of undesirable and serious post-surgical fibrous adhesions.

In the case when the anti-adhesion material comprises a bioabsorbable material, it is preferable to choose a bioabsorbable material that is absorbed only after a few days, so as to ensure that the anti-adhesion coating can perform its function of protecting the surrounding organs during the days after the operation and until the cell recolonization of the prosthesis in turn protects these organs.

In one embodiment, the anti-adhesion coating is in the form of a bioabsorbable film.

In one embodiment, the anti-adhesion coating is in the form of a bioabsorbable film that likewise covers the marking means, which is itself formed from a bioabsorbable material. Thus, once the anti-adhesion coating has been bioabsorbed, the marking means can in turn be bioabsorbed. This avoids an excessive amount of foreign material remaining in the patient's body once the cell recolonization of the prosthesis has taken place.

The advantages of the present invention will become clearer from the following description and from the attached drawings, in which:

FIG. 1 is a top view of a prosthesis according to the invention,

FIG. 2 is a top view of a variant of the marking means of the prosthesis of FIG. 1.

Referring to FIG. 1, this shows a prosthesis 1 according to the invention seen from above. The prosthesis 1 is intended for the repair of a hernia, in particular as a reinforcement of the abdominal wall, one of its faces being intended to be placed facing the abdominal wall, and its opposite face being intended to be placed facing the abdominal cavity. The prosthesis 1 comprises a patch 2 made of biocompatible material, in the form of an openworked textile in the example shown. An openworked textile of this kind can be obtained by the methods described in the documents WO99/05990, WO2009/031035 and WO2009/071998. The textile forming the patch 2 of the prosthesis according to the invention can be made of bioabsorbable yarns, of non-bioabsorbable yarns, or of a combination of bioabsorbable yarns and non-bioabsorbable yarns. For example, this textile is produced using yarns that are white in colour, for example non-bioabsorbable monofilament yarns of polyethylene terephthalate (PET) with a diameter of 90 µm, such that the patch 2 is likewise white in colour.

The patch 2 has a generally plane geometric shape that defines said two opposite faces, only one of these faces, i.e. the face 2a intended to be placed facing the abdominal cavity, being visible in FIG. 1.

In the example shown in FIG. 1, the patch 2 has a generally rectangular shape with a length L, in its longitudinal direction D, a width I, and a centre C. For example, the length L can be up to 42 cm, and the width I can be up to 32 cm.

The patch 2 is provided, on its face 2a, with a marking means in the form of an element 3 which is a sheet of material composed of a biocompatible textile. Alternatively, the sheet of material could be a film of biocompatible material, obtained by extrusion for example.

In embodiments not shown, the element 3 in the form of a sheet of material could be replaced by an element obtained by depositing, on the face 2a of the patch 2, a coating of a biocompatible material, for example an ink, collagen, or any other natural or synthetic polymer, either absorbable or non-absorbable; for example, this deposit could be obtained by applying the face 2a to the element, which is in solution before forming a gel. Alternatively, the element could be applied by being sprayed or painted onto the face in question, for example in the case of an ink.

In the example shown, the element 3 is formed by a textile. This textile can be identical to or different than the one constituting the patch 2. In the example shown, the textile forming the element 3 differs from that forming the patch 2. In particular, the textile forming the element 3 has a different colour than the white colour of the patch 2. For example, the textile forming the element 3 can be made of green-coloured non-bioabsorbable monofilament yarns of polyethylene terephthalate (PET) with diameter 90 µm. Therefore, in this example, the element 3 is non-bioabsorbable.

Alternatively, the textile forming the element 3 can be made of bioabsorbable yarns.

As will be seen from FIG. 1, the element 3 has a shape whose perimeter combines the contours of a circular shape 4 and of a generally elongate shape 5, which is attached to said circular shape 4. As is shown in FIG. 1, the circular shape 4 has generally the shape of a ring, its central part 4a being without material. The absence of material in the central part 4a results in a difference in colour in relation to the rest of the circular shape 4, thus making it possible to quickly locate the central point 4b of the circular shape, which central point 4b of the circular shape is coincident with the centre C of the patch 2 in the example shown. Thus, the absence of material in the central part 4a of the circular shape 4 constitutes a means for identifying the central point 4b of the circular shape and, accordingly, the centre C of the patch 2 which, in the example shown, also corresponds to the centre of the prosthesis 1.

In the example shown, the elongate shape 5 has generally the shape of an elongate triangle, or of an arrow, such that its longitudinal axis A is parallel to the longitudinal direction D of the patch 2, in the plane of the patch 2. In the example shown, the elongate shape 5 is attached to said circular shape 4 via one of its ends. FIG. 2 shows a variant of the element 3, in which the elongate shape 5 has the shape of an elongate rectangle and is attached to the circular shape 4 via one of its long sides.

The elongate shape 5 of the element 3 thus makes it possible to determine automatically the longitudinal direction D of the prosthesis 1, even if only a small portion of the prosthesis 1 is visible, namely a limited portion corresponding to its central region, without seeing the edges of the prosthesis.

Thus, the element 3 is situated inside a central region 6 (indicated by broken lines in FIG. 1) of said patch 2, the surface area of said central region 6 being less than or equal to 20 cm$^2$, preferably less than or equal to 16 cm$^2$, more preferably less than or equal to 7 cm$^2$.

When fitting the prosthesis 1 in place by laparoscopy, the surgeon, whose field of view is limited on account of the operating technique, cannot see the edges of the prosthesis 1, since they are situated outside his field of view. By contrast, he can see the whole of the element 3. The specific shape of this element 3 provides him with all of the following information at one glance:
- the face with which he is dealing: the surgeon knows, before implanting the prosthesis, that the marking means, namely the element 3, is situated on that face of the patch 2 intended to be placed facing the abdominal cavity;
- the centre of the patch 2, corresponding to the centre of the prosthesis: the means for identifying the central point 4b of the circular shape 4, namely the absence of material 4a, by colour contrast shows the surgeon the centre of the patch 2;
- the longitudinal direction of the patch 2, by means of the longitudinal axis A of the elongate shape 5.

The surgeon thus has all the information he needs in order to position the prosthesis 1 correctly, without having to move the prosthesis 1 about to look for means of information situated at the periphery of the latter.

In the example shown, the element 3 is sewn onto the textile face 2a of the patch 2. Alternatively, it could be glued onto this face 2a.

In an example not shown, the patch 2, on its face 2a provided with the element 3, is covered with an anti-adhesion coating, said coating likewise covering the element 3.

Such a coating makes it possible to limit or avoid the formation of post-surgical adhesions after implantation of the prosthesis. For example, this anti-adhesion coating is in the form of a bioabsorbable collagen film, as described in WO9906080.

The prosthesis according to the invention allows a surgeon, when implanting a hernia prosthesis having a longitudinal dimension, to see at one glance the whole of a marking means for indicating to the surgeon the face of the prosthesis to be placed facing the abdominal cavity, the longitudinal direction of the prosthesis, and the centre of the prosthesis. The manoeuvres involved in positioning the prosthesis in relation to the defect to be treated and to the surrounding organs are greatly facilitated.

The invention claimed is:

1. A prosthesis comprising a first textile made of a first biocompatible material, said first textile having a first generally plane geometric shape that defines a first face and a second face opposite the first face, said first face including a central region surrounding a center on said first face, said central region having a surface area smaller than a surface area of said first face, and a second open-worked textile made of a second biocompatible material, said second open-worked textile positioned on the first face of the first textile, said second open-worked textile having a second generally plane geometric shape including an outer perimeter situated inside the central region of the first face of the first textile and designed to indicate both the center and a longitudinal direction of the first face of the first textile, said second open-worked textile including a part absent of material, the part located on the center of the first face of the first planar textile.

2. The prosthesis according to claim 1, wherein the first textile is an open-worked textile.

3. The prosthesis according to claim 1, wherein the first textile is a three-dimensional textile.

4. The prosthesis according to claim 3, wherein the second open-worked textile is a two-dimensional knit.

5. The prosthesis according to claim 1, wherein the first biocompatible material is a bioabsorbable material.

6. The prosthesis according to claim 5, wherein the second biocompatible material is a non-bioabsorbable material.

7. The prosthesis according to claim 1, wherein the first generally plane geometric shape of the first textile is generally parallel to the second generally plane geometric shape of the second open-worked textile.

8. The prosthesis according to claim 1, wherein the outer perimeter of the shape of second open-worked textile combines a circular shape and a generally elongate shape attached to said circular shape.

9. The prosthesis according to claim 8, wherein a longitudinal axis of the elongate shape is parallel to the longitudinal direction of the first face of the first textile.

10. The prosthesis according to claim 8, wherein the elongate shape is an elongate triangle.

11. The prosthesis according to claim 10, wherein the elongate shape is attached to the circular shape via one end of an elongate triangle.

12. The prosthesis according to claim 8, wherein the elongate shape is an elongate rectangle.

13. The prosthesis according to claim 12, wherein the elongate rectangle is attached to the circular shape via a long side of the elongate rectangle.

14. The prosthesis according to claim 8, wherein the circular shape is a ring.

15. The prosthesis according to claim 8, wherein the part absent of material of the second open-worked textile is a central part of the circular shape.

16. The prosthesis according to claim 1, wherein the second open-worked textile has a color different than a color of the first textile.

17. The prosthesis according to claim 1, wherein the second open-worked textile is sewn or glued onto the first face of the first textile.

18. The prosthesis according to claim 1, wherein the surface area of the central region is less than or equal to 20 $cm^2$.

19. The prosthesis according to claim 1, wherein the first or second face further comprises an anti-adhesion coating.

20. The prosthesis according to claim 19, wherein said anti-adhesion coating covers said second open-worked textile.

* * * * *